United States Patent [19]

Sugiyama et al.

[11] Patent Number: 5,036,834
[45] Date of Patent: Aug. 6, 1991

[54] ILLUMINATING LIGHT INTRODUCING DEVICE FOR ENDOSCOPE

[75] Inventors: Akira Sugiyama; Rensuke Adachi; Hiroshi Sano, all of Tokyo, Japan

[73] Assignee: Asahi Kogaku Kogyo Kabushiki Kaisha, Tokyo, Japan

[21] Appl. No.: 524,971

[22] Filed: May 18, 1990

[30] Foreign Application Priority Data

May 23, 1989 [JP] Japan .................. 1-59864[U]

[51] Int. Cl.⁵ .............................................. A61B 1/00
[52] U.S. Cl. ..................................... 128/6; 385/117; 385/119
[58] Field of Search .................. 128/4, 6, 23; 350/96.26

[56] References Cited

U.S. PATENT DOCUMENTS

| | | | |
|---|---|---|---|
| 2,932,294 | 4/1960 | Fourestier et al. | 128/6 |
| 3,357,433 | 12/1967 | Fourestier et al. | 128/4 X |
| 4,286,585 | 9/1981 | Ogawa | 128/6 |
| 4,294,234 | 10/1981 | Matsuo | 128/6 |
| 4,529,267 | 7/1985 | Nishioka et al. | 350/96.26 |
| 4,874,220 | 10/1989 | Yamagata | 350/96.26 |

FOREIGN PATENT DOCUMENTS 63-200811 12/1988 Japan .

Primary Examiner—William H. Grieb
Attorney, Agent, or Firm—Sandler, Greenblum & Bernstein

[57] ABSTRACT

A device for introducing illuminating light that is emitted from a light source to an illuminating light guide fiber bundle associated with an endoscope. The device has an incident end face of the light guide fiber bundle that is disposed at a position where the light from the light source is converged, and a lens which is disposed in close proximity to the incident end face of the light guide fiber bundle. That lens has a convex surface which faces the light source and a concave surface which faces the light guide fiber bundle.

Accordingly, the illuminating light is refracted by the concave surface of the lens so as to enter the light guide fiber bundle at a small angle to the optical axis. Thus, the illuminating light is transmitted through the light guide fiber bundle with a considerably small number of times of reflection.

10 Claims, 2 Drawing Sheets

ILLUMINATING LIGHT INTRODUCING DEVICE FOR ENDOSCOPE

BACKGROUND OF THE INVENTION

1. Field of the Invention

The present invention relates to a device for introducing light that is emitted from a light source lamp to an illuminating light guide fiber bundle of an endoscope.

Generally, the incident end faces of light guide fiber bundles of endoscopes have an exceedingly small area. It is therefore necessary to condense light that is emitted from a light source lamp into a small spot of light and to dispose the incident end face of a light guide fiber bundle at a point where the light is converged so that the quantity of light that enters the light guide fiber bundle is maximized.

However, it is difficult to converge the illuminating light on the incident end face of the light guide fiber bundle in complete spot-like form because the light source lamp has a certain size of its own.

2. Description of the Prior Art

FIG. 4 shows a conventional illuminating light introducing device, in which a convex lens 51 is disposed in close proximity to an incident end face 52c of a light guide fiber bundle 52 with a view to maximizing the quantity of light that enters the light guide fiber bundle 52.

In the conventional illuminating light introducing device, however, the one of the two surfaces 51a and 51b of the convex lens 51 that faces the incident end face 52c of the light guide fiber bundle 52, i.e., the surface 51b, is a planar surface and consequently the light that is refracted by the convex surface 51a enters each of the optical fibers comprising the light guide fiber bundle 52 at a large angle of incidence.

As a result, the illuminating light is reflected an exceedingly large number of times inside each of a multiplicity of optical fibers 152 comprising the light guide fiber bundle 52, as shown in FIG. 5. Accordingly, the transmitted light is gradually attenuated as it is repeatedly reflected, resulting in a marked reduction in the quantity of illuminating light that is applied to an object of observation.

SUMMARY OF THE INVENTION

An object of the present invention is to provide an illuminating light introducing device for an endoscope which is capable of minimizing the loss of the light quantity during the transmission of illuminating light through a light guide fiber bundle of the endoscope.

Other objects and advantages of the present invention will become apparent from the following detailed description of an illustrated embodiment of the invention.

According to the present invention, there is provided a device for introducing illuminating light that is emitted from a light source to an illuminating light guide fiber bundle associated with an endoscope, comprising: an incident end face of the light guide fiber bundle that is disposed at a position where the light from the light source is converged; and a lens which is disposed in close proximity to the incident end face of the light guide fiber bundle, the lens having a convex surface which faces the light source and a concave surface which faces the light guide fiber bundle.

BRIEF DESCRIPTION OF THE DRAWINGS

The present invention may be more fully understood from the description of a preferred embodiment of the invention set forth below, together with the accompanying drawings, in which.

DESCRIPTION OF THE EMBODIMENT

One embodiment of the present invention will be described below with reference to the accompanying drawings.

Figure 1:
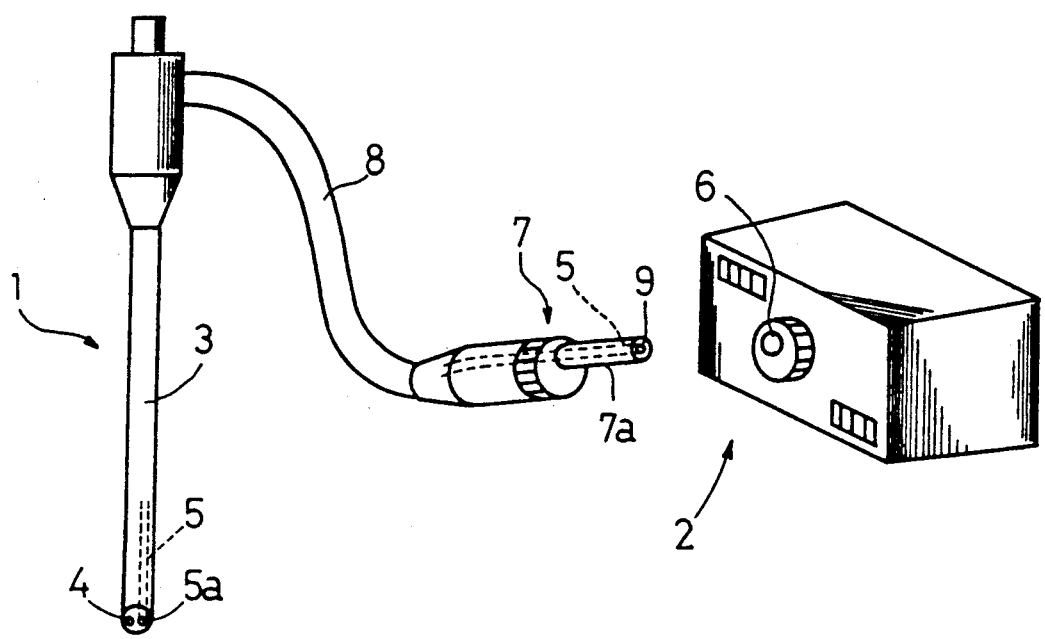
FIG. 1 is a perspective view of an endoscope and an associated light source device in one embodiment of the present invention.

FIG. 1 schematically shows an endoscope 1 and a light source device 2 in the embodiment.

An observation window 4 and an emergent end face 5a of an illuminating light guide fiber bundle 5 are disposed side by side at the distal end of an insert part 3 of the endoscope 1.

A connector rod 7a projects from a connector 7, which is provided at the end of a flexible connecting tube 8. An incident end portion of the light guide fiber bundle 5 is disposed at the tip of the connector rod 7a. A lens 9 is disposed in the tip of the connector rod 7a, the lens 9 facing the incident end face 5c of the light guide fiber bundle 5.

The light source device 2 is formed with a connector socket 6, to which the connector 7 is detachably connected.

Figure 2:
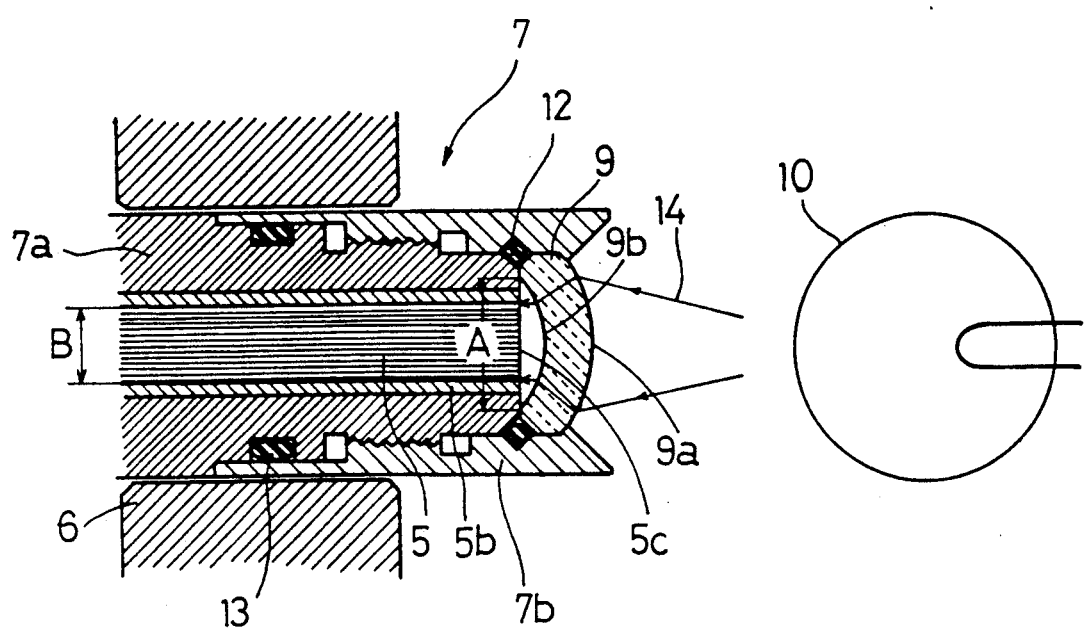
FIG. 2 is a sectional view of an illuminating light introducing device according to the embodiment.

FIG. 2 shows the connector 7 which is connected to the connector socket 6. A light source lamp 10 is disposed inside the light source device 2 shown in FIG. 1. The flat incident end face 5c of the light guide fiber bundle 5 is disposed at a position where light that is emitted from the light source lamp 10 is converged. The incident end portion of the light guide fiber bundle 5 is screwed or bonded to the tip of the connector rod 7a, which is inserted into the connector socket 6. A tubular cap 5b surrounds the light guide fiber bundle 5.

A cap 7b is in thread engagement with the tip of the connector rod 7a. The lens 9 is accommodated within the cap 7b.

The lens 9 has a larger diameter than the diameter of the incident end face 5c of the light guide fiber bundle 5. The lens 9 has a convex surface 9a which faces the light source lamp 10, and a concave surface 9b which faces the flat incident end face 5c of the light guide fiber bundle 5 as shown in FIG. 2.

In this embodiment, the convex and concave surfaces 9a and 9b of the lens 9 have the same curvature radius, so that the calculation of an optical path is facilitated. The diameter A of the concave surface 9b is greater than the diameter B of the incident end face 5c of the light guide fiber bundle 5. The diameter A may, however, be equal to the diameter B, i.e., $A \geqq B$.

Waterproof sealing O-rings 12 and 13 prevent water from entering the space defined between the lens 9 and the incident end face 5c of the light guide fiber bundle 5.

In this embodiment, light that is emitted from the light source lamp 10 is refracted by the convex surface 9a of the lens 9 at a large angle to the optical axis so as to converge on the incident end face 5c of the light guide fiber bundle 5. However, just before entering the light guide fiber bundle 5, the light is refracted by the concave surface 9b of the lens 9 so as to enter the incident end face 5c of the light guide fiber bundle 5 at a small angle to the optical axis.

Figure 3:
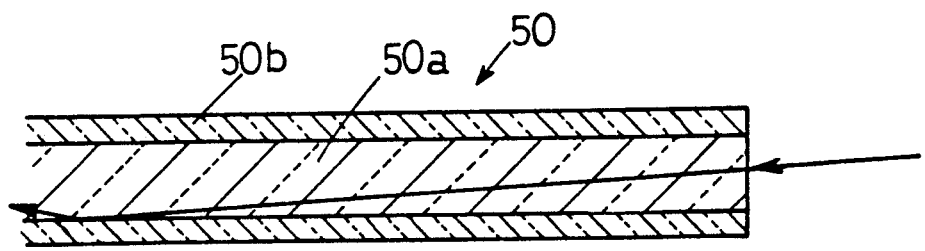
FIG. 3 schematically shows the way in which illuminating light is transmitted through one of the optical fibers comprising a light guide fiber bundle in the embodiment.
Figure 4:
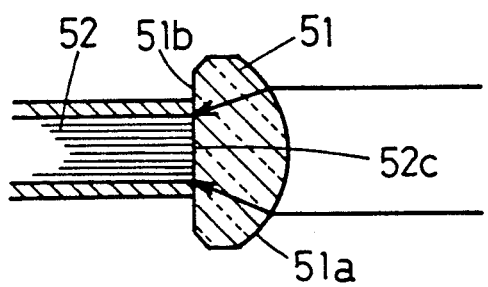
FIG. 4 is a fragmentary sectional view of a conventional illuminating light introducing device for an endoscope.
Figure 5:
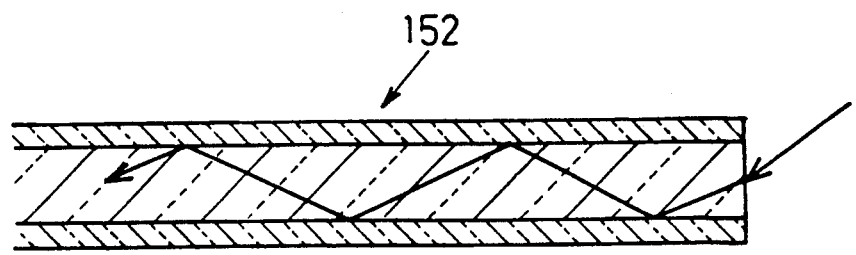
FIG. 5 schematically shows the way in which illuminating light is transmitted through one of the optical fibers comprising a light guide fiber bundle in the prior art.

Accordingly, the illuminating light is transmitted through each of the optical fibers 50 comprising the light guide fiber bundle 5 with a considerably small number of times of reflection, as shown in FIG. 3, and emitted toward the object from the emergent end face 5a of the light guide fiber bundle 5, which is shown in FIG. 1. In FIG. 3, reference numerals 50a and 50b denote a core and a cladding of the optical fiber 50.

According to the present invention, illuminating light is refracted by the convex surface of the lens and a large quantity of light can therefore be applied to the light guide fiber bundle. Just before entering the light guide fiber bundle, the illuminating light is refracted by the concave surface of the lens so as to enter the light guide fiber bundle at a small angle to the optical axis. Thus, the illuminating light is transmitted through the light guide fiber bundle with a considerably small number of times of reflection.

Accordingly, the attenuation of illuminating light in the light guide fiber bundle is minimized, so that excellent observation can be performed with a large quantity of illuminating light even in the case of an endoscope that has a light guide fiber bundle with a relatively small diameter.

While the invention has been described by reference to a specific embodiment chosen for purposes of illustration, it should be apparent that numerous modifications could be made thereto by those skilled in the art without departing from the basic concept and scope of the invention.

We claim:

1. A device for introducing illuminating light that is emitted from a light source to an illuminating light guide fiber bundle associated with an endoscope, comprising:
   a flat incident end face of said light guide fiber bundle; and
   a lens which is disposed in close proximity to said flat incident end face of said light guide fiber bundle, said lens having a convex surface which faces said light source and a concave surface which faces said flat incident end face of said light guide fiber bundle, wherein a space is formed between said concave surface and said flat incident end face.

2. An illuminating light introducing device according to claim 1, wherein said incident end face of said light guide fiber bundle is disposed at a position where the light from said light source is converged.

3. An illuminating light introducing device according to claim 1, wherein the diameter of the concave surface of said lens is not smaller than the diameter of the incident end face of said light guide fiber bundle.

4. An illuminating light introducing device according to claim 1, wherein the convex and concave surfaces of said lens have the same curvature radius.

5. An illuminating light introducing device according to claim 1, wherein a waterproof sealing means is provided between the incident end face of said light guide fiber bundle and said lens.

6. An illuminating light introducing device for an endoscope, which is provided in a connector that is detachably connected to a light source device, to apply light that is emitted from a light source lamp provided in said light source device to an illuminating light guide fiber bundle associated with said endoscope, comprising:
   a flat incident end face of said light guide fiber bundle; and
   a lens which is disposed in close proximity to said incident end face of said light guide fiber bundle, said lens having a convex surface which faces said light source lamp and a concave surface which faces said flat incident end face of said light guide fiber bundle, wherein a space is formed between said concave surface and said flat incident end face.

7. An illuminating light introducing device according to claim 6, wherein said incident end face of said light guide fiber bundle is disposed at a position where the light from said light source lamp is converged.

8. An illuminating light introducing device according to claim 6, wherein the incident end face of said light guide fiber bundle and said lens are disposed in the tip of a rod that projects from said connector.

9. A device for introducing illuminating light to an illuminating light guide fiber bundle, comprising:
   a flat incident end face of said light guide fiber
   a lens which is disposed in close proximity to said incident end face of said light guide fiber bundle, said lens having a convex surface which faces a light source and a concave surface which faces said flat incident end face of said light guide fiber bundle, wherein a space is formed between said concave surface and said flat incident end face.

10. An illuminating light introducing device according to claim 9, wherein said incident end face of said light guide fiber bundle is disposed at a position where the light from said light source is converged.

* * * * *

UNITED STATES PATENT AND TRADEMARK OFFICE
CERTIFICATE OF CORRECTION

PATENT NO. : 5,036,834
DATED : August 6, 1991
INVENTOR(S) : A. SUGIYAMA et al.

It is certified that error appears in the above-indentified patent and that said Letters Patent is hereby corrected as shown below:

At column 4, line 44 (claim 9, line 3), after "fiber" insert --- bundle; and---.

Signed and Sealed this

Twelfth Day of April, 1994

*Attest:*

BRUCE LEHMAN

*Attesting Officer*

Commissioner of Patents and Trademarks